United States Patent [19]

Payne

[11] Patent Number: 4,486,220

[45] Date of Patent: Dec. 4, 1984

[54] 6-OXATRICYCLO[3.2.1.1$^{3,8}$]NONAN-4-OL ETHERS AND COMPOSITIONS AND METHODS FOR THE REGULATION OF PLANT GROWTH

[75] Inventor: George B. Payne, Modesto, Calif.

[73] Assignee: Shell Oil Company, Houston, Tex.

[21] Appl. No.: 486,124

[22] Filed: Apr. 18, 1983

[51] Int. Cl.$^3$ .................. A01N 43/12; C07D 307/00
[52] U.S. Cl. ........................................ 71/88; 71/90;
71/92; 71/94; 71/95; 544/238; 546/139;
546/152; 546/180; 546/269; 548/134; 548/203;
548/206; 548/235; 548/249; 548/262; 548/336;
548/525; 548/374; 549/60; 549/459
[58] Field of Search ............ 549/459, 60; 71/88,
71/94, 90, 92, 95; 546/269, 139, 152, 180;
548/134, 203, 206, 235, 249, 262, 336, 525, 374;
544/238

[56] References Cited

U.S. PATENT DOCUMENTS 3,346,596 10/1967 Hoch et al. ................ 260/346.1
3,419,380 12/1968 Hoch et al. ..................... 71/88
3,661,998 5/1972 Hoch ........................... 260/586
3,821,307 6/1974 Hoch ........................... 260/586

FOREIGN PATENT DOCUMENTS 6414006 12/1963 Netherlands.

Primary Examiner—Henry R. Jiles
Assistant Examiner—Bernard I. Dentz

[57] ABSTRACT

Compounds of the formula

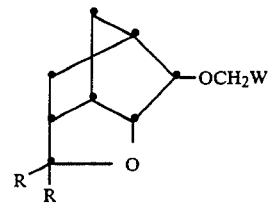

wherein each R is H or alkyl and W is an optionally substituted unsaturated group, a cycloalkyl group, a secondary alkyl group, an aromatic group or a heterocyclic group, are useful as plant growth regulators and herbicides.

11 Claims, No Drawings

6-OXATRICYCLO[3.2.1.1$^{3,8}$]NONAN-4-OL ETHERS AND COMPOSITIONS AND METHODS FOR THE REGULATION OF PLANT GROWTH

BACKGROUND OF THE INVENTION

Field of the Invention

The present invention relates to novel 6-oxatricyclo[3.2.1.1$^{3,8}$]nonan-4-ol ethers, their use as plant growth regulators and herbicides and to compositions containing these ethers.

Summary of the Invention

The present invention is directed to novel 6-oxatricyclo[3.2.1.1$^{3,8}$]nonan-4-ol ethers of formula I

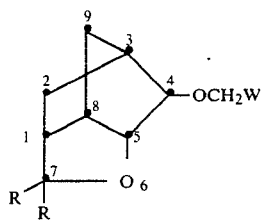

wherein each R is independently a hydrogen atom or an alkyl group containing from 1 to 6 carbon atoms; and W is an optionally substituted unsaturated group containing up to 4 carbon atoms, a cycloalkyl group containing 3 to 10 carbon atoms, a secondary alkyl group containing 3 to 10 carbon atoms, an aromatic group containing up to 14 carbon atoms or a heterocyclic group containing up to 14 carbon atoms. The compounds are useful as herbicides, plant growth regulators and the like, as will be further discussed below.

Optional substituents for W in the ethers of formula I above include halogen atoms of an atomic number of 9 to 35, inclusive, or alkyl of 1 to 4 carbon atoms, alkoxy of 1 to 4 carbon atoms or alkylthio of 1 to 4 carbon atoms each optionally substituted by one or more halogen atoms, or equivalent kinds of substituents.

In the ethers of formula I, preferably, each R is independently a hydrogen atom or a methyl group. In one embodiment of the invention, each R is preferably a hydrogen atom.

In the ethers of formula I, preferably, W is an ethynyl group, a 2-pyridinyl group or a phenyl group optionally substituted by 1 or 2 chlorine or fluorine atoms or methyl groups. In one embodiment of the invention, W is a 2,6-dichlorophenyl, a phenyl, a 2-fluorophenyl or a 2-methylphenyl group.

Non-limiting species of the derivatives of formula I include 4-(2-propynyloxy)-7,7-dipropyl-6-oxatricyclo[3.2.1.1$^{3,8}$]nonane, 4-(2-methylbenzyloxy)-7,7-dimethyl-6-oxatricyclo[3.2.1.1$^{3,8}$]nonane, 4-(2-chlorobenzyloxy)-7,7-diethyl-6-oxatricyclo[3.2.1.1$^{3,8}$]nonane, 4-(3-pyridazinylmethoxy)-7,7-dimethyl-6-oxabicyclo[3.2.1.1$^{3,8}$]nonane, 4-(2-bromobenzyloxy)-6-oxatricyclo[3.2.1.1$^{3,8}$]nonane, and the like.

Compounds that possess substantially the same plant growth regulator or herbicidal utility as those described herein and which can be prepared in like manner are equivalents thereof and include compounds wherein, for example, W is an unsaturated, aromatic or heterocyclic moiety, or cyclopropyl or 1-methylcyclopropyl, including but not limited to cyano, naphthyl, imidazolyl, triazolyl, thiadiazolyl, 2-quinolinyl, 1-isoquinolinyl, pyrrolyl, cyclohexenyl, N-methylimidazol-2-yl, N-methylpyrazol-2-yl, isoxazolyl, oxazolyl, isothiazolyl, thiazolyl, thienyl, 5-methyl-2-furanyl, and the like.

The ethers of formula I of the invention exhibit geometrical and optical isomerism and may be prepared in geometrical and/or optical forms, and as racemates. The various individual optical and geometrical forms and various combinations of the derivatives of the invention usually have some difference in herbicidal or plant growth control properties. The present invention contemplates all these active forms. The ethers of formula I that have the WCH$_2$O group in the beta-orientation (cis with respect to the ring oxygen when viewed as substituents on the 1,2,3,4,5,8-cyclohexane unit) usually have the highest activity. Moreover, the ethers of the formula I of the invention also are useful as solvents or dispersing agents, e.g. for paints, pigments, polymers and synthetic fibers, and as plasticizers, e.g. for vinyl resins. These latter uses are irrespective of stereoisomerism.

The ethers of formula I of the invention are prepared by an etherification reaction which introduces the group CH$_2$W. The etherification is conducted by treating the corresponding 6-oxatricyclo[3.2.1.1$^{3,8}$]nonan-4-ol with a compound of the formula WCH$_2$X in which W is defined as in formula I above and X is a halogen atom, such as bromine, chlorine or iodine, or is a mesyloxy, tosyloxy group or the like, in the presence of a base and, preferably, an inert diluent. The base is suitably an alkali metal hydride, hydroxide or carbonate, including, for example, sodium hydride, sodium hydroxide, potassium carbonate and the like. Inert diluents (solvents) are suitably organic solvents, such as ethers, aromatic hydrocarbons and the like, including for example, diethyl ether, tetrahydrofuran, dimethyl sulfoxide, toluene, methylene chloride and the like. The reaction is usually carried out under normal pressures and ambient temperatures. Suitable temperatures of the reaction include those from about 0° C. to about 120° C., preferably from about 20° C. to about 100° C. The reaction can be conducted in a two-phase system, preferably in the presence of a phase-transfer catalyst. For example, such a system is an aqueous sodium or potassium hydroxide solution with toluene or methylene chloride with a catalyst, such as an ammonium compound, including tetra-n-butylammonium chloride, bromide or hydrogen sulfate, triethylbenzylammonium chloride and the like.

The ethers of formula I are recovered and isolated by conventional techniques.

The corresponding 6-oxatricyclo[3.2.1.1$^{3,8}$]nonan-4-ols and 6-oxatricyclo[3.2.1.1$^{3,8}$]nonan-4-ones are also novel and have the formula II

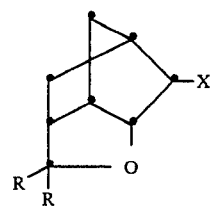

wherein each R is independently a hydrogen atom or an alkyl group containing from 1 to 6 carbon atoms; and X is —OH or =O. In the novel compounds of formula II, preferably, each R is independently a hydrogen atom or a methyl group. In one embodiment of the invention, each R is a hydrogen atom.

The compounds of formula II are prepared by multi-step conventional procedures from ethyl bicyclo[2.2.1-]hept-5-ene-2-carboxylate, a known Diels-Alder adduct of ethyl acrylate and cyclopentadiene.

When R is hydrogen, this adduct is reduced to the corresponding known bicyclo[2.2.1]hept-5-ene-2-methanol by conventional reduction procedures, such as use of sodium metal and an alcohol or use of lithium aluminum hydride and the like. However, when R is an alkyl group, this adduct is treated by conventional procedures to form tertiary alcohols with a Grignard reagent, RMgX, in which R is the desired alkyl substituent as defined in formulas I or II and X is a halogen, such as bromine.

Regardless of which of the two ways described above in which the adduct is first treated, the resulting product is oxidized with a conventional oxidizing agent, such as m-chloroperbenzoic acid, to the corresponding 6-oxatricyclo[3.2.1.1$^{3,8}$]nonan-4-ol. This alcohol can be etherified directly. However, when this alcohol is prepared in predominately the alpha-form, as is the case when m-chloroperbenzoic acid is used, it can be converted to the beta-form by conventional procedures, such as oxidation with oxalyl chloride-dimethyl sulfoxide or the like, followed by treating the resulting 6-oxatricyclo[3.2.1.1$^{3,8}$]nonan-4-one with suitable reducing agents such as sodium borohydride, to obtain the desired 6-oxatricyclo[3.2.1.1$^{3,8}$]nonan-4-ol in the beta-form.

ILLUSTRATIVE EMBODIMENTS

The invention is illustrated by the following embodiments which describe the preparation of typical species of the invention. These embodiments are presented for the purpose of illustration only, and should not be regarded as limiting the invention in any way. The identity of the products, including intermediates, was confirmed by elemental, infrared and nuclear magnetic resonance spectral (NMR) analyses as necessary.

EMBODIMENT I

6-Oxabicyclo[2.2.1]nonan-4-one

To a stirred solution of 12.4 g of bicyclo[2.2.1]hept-5-ene-2-methanol (Matheson, Coleman and Bell; b.p. 60° C. (1 mm)) in 150 ml of diethyl ether was added portionwise <10° C. 20.4 g of m-chloroperbenzoic acid. After 2.5 hours, the cooling bath was removed and the solution was stirred at 25° C. for 1 hour. The mixture was diluted with 100 ml of diethyl ether and treated portionwise <30° C. with 30 g of calcium hydroxide. After filtration through filter aid, the filtrate was washed with 50 ml of water, dried, and vacuum concentrated to 12.5 g of an amorphous residue of 6-oxatricyclo[3.2.1.1$^{3,8}$]nonan-4α-ol. This was oxidized by oxalyl chloride-dimethylsulfoxide-triethylamine according to the procedure of Omura and Swern, *Tetrahedron*, 34, 1651 (1978), to give 11.9 g of relatively pure ketone as a bottoms product (oil).

EMBODIMENT II

6-Oxatricyclo[3.2.1.1$^{3,8}$]nonan-4α-ol

To a stirred solution of 4.7 g of the ketone of Embodiment I in 50 ml of t-butanol was added 1.3 g of sodium borohydride. The exothermic reaction carried to 47° C. After 4 hours at 25° C., 50 ml of water was added and the mixture was extracted three times with 75 ml portions of methylene chloride. The combined methylene chloride extracts were washed, dried and concentrated to the product as a solid residue of 4.3 g, m.p. ca 170°–180° C.

EMBODIMENT III

4α-Benzyloxy-6-oxatricyclo[3.2.1.1$^{3,8}$]nonane

To a stirred solution of 2.8 g of the alcohol of Embodiment II in 30 ml of N,N-dimethylacetamide was added 1.1 g of 50% sodium hydride (washed with hexane). After 0.5 hour at 25° C. and 0.5 hour at 60° C., the mixture was cooled to 25° C. and treated with 2.8 g of benzyl chloride. After 18 hours at ambient temperature and 0.5 hour at 50° C., the mixture was cooled, poured into water and extracted twice with methylene chloride. The combined methylene chloride extracts were washed, dried, concentrated and Claisen-distilled to give 3.9 g of product, b.p. 107° C. (0.1 mm).

EMBODIMENTS IV–VII

Following procedures similar to those described in Embodiment III above, additional 6-oxatricyclo[3.2.1.1$^{3,8}$]nonan-4β-ol ethers set forth in Table I below were prepared.

TABLE I

6-OXATRICYCLO[3.2.1.1$^{3,8}$]NONAN-4β-OL ETHERS

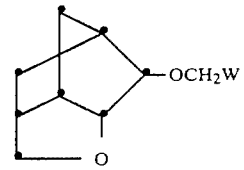

| Embodiment | W | b.p., °C. | (mm) |
|---|---|---|---|
| IV | 2-F—phenyl | 104° C. | (0.1) |
| V | 2-CH$_3$—phenyl | 110° C. | (0.1) |
| VI | 2,6-Cl$_2$—phenyl | 135° C. | (0.1) |
| VII | 2-pyridinyl | 124–126 | (0.15) |

EMBODIMENT VIII

Ethyl Bicyclo[2.2.1]hept-5-ene-2-carboxylate

To a stirred 200 ml portion of absolute ethanol previously warmed to 65°–70° C. was added in a thin stream 24.3 g of 5-norbornene-2-carbonyl chloride. After 0.5 hour longer at reflux, the mixture was vacuum-concentrated to low volume. The residue was dissolved in methylene chloride and washed with saturated sodium bicarbonate. After drying, distillation gave 17.3 g of product, b.p. 80°–85° C. (10 mm).

EMBODIMENT IX

α,α-Dimethylbicyclo[2.2.1]hept-5-ene-2-methanol

To a stirred mixture of 48 ml of 2.95N methyl magnesium chloride in tetrahydrofuran and 100 ml of tetrahydrofuran was added dropwise at 30°–35° C. a solution of 8.3 g of the ester of Embodiment VIII in 25 ml of tetrahydrofuran. After 0.5 hour longer at 50° C., the mixture was cooled and treated carefully with 100 ml of water and then 50 ml of saturated sodium bicarbonate. The resulting mixture of liquid and solid was extracted three times with diethyl ether and the combined ether extracts were dried, concentrated and Claisen-distilled to give 6.4 g of product, b.p. 89°–91° C. (14 mm).

EMBODIMENT X 7,7-Dimethyl-6-oxatricyclo[3.2.1.1$^{3,8}$]nonan-4α-ol

Oxidation of 9.4 g of the alcohol of Embodiment IX with 13.8 g of m-chloroperbenzoic acid was carried out as an Embodiment I with bicyclo[2.2.1]hept-5-ene-2-methanol to give 6.0 g of product, b.p. 105°–107° C. (1.5 mm), that solidified on cooling.

EMBODIMENT XI 7,7-Dimethyl-6-oxatricyclo[3.2.1.1$^{3,8}$]nonan-4-one

The oxidation of 7.9 g of the alcohol of Embodiment X was carried out as in Embodiment I by the procedure of Omura and Swern to give 6.2 g of product, b.p. 93°–100° C. (1.5 mm).

EMBODIMENT XII 7,7-Dimethyl-6-oxatricyclo[3.2.1.1$^{3,8}$]nonan-4β-ol

Sodium borohydride reduction of the ketone of Embodiment XI was carried out as for the preparation of Embodiment II to give the product, b.p. 66°–70° C. (1.0 mm).

EMBODIMENT XIII

4β-Benzyloxy-7,7-dimethyl-6-oxatricyclo[3.2.1.1$^{3,8}$]nonane

The benzylation of the alcohol of Embodiment XII was carried out as for the preparation of Embodiment III to give the product, b.p. 108°–110° C. (0.1 mm).

The invention includes a method of regulating plant growth, including combating unwanted plants, which comprises applying to the locus an effective amount of a compound of Formula I. For example, the compounds can change plant morphology, depress the growth of plants or kill plants. As herbicides, they appear to be more effective when applied preemergence or pre-plant incorporated, particularly to control grassy weeds. For application, the compound generally is applied most effectively by formulating it with a suitable inert carrier or surface-active agent, or both. The invention, therefore, also includes compositions suitable for regulating plant growth, including combating unwanted plants, such compositions comprising an inert carrier or surface-active agent, or both, and as active ingredient at least one compound of formula I.

The term "carrier" as used herein means an inert solid or fluid material, which may be inorganic or organic and of synthetic or natural origin, with which the active compound is mixed or formulated to facilitate its application to the plant, seed, soil or other object to be treated, or its storage, transport and/or handling. Any of the materials customarily employed in formulating pesticides, herbicides, or fungicides, are suitable.

Suitable solid carriers are natural and synthetic clays and silicates, for example, natural silicas such as diatomaceous earths; magnesium silicates, for example, talcs; magnesium aluminum silicates, for example, attapulgites and vermiculites; aluminum silicates, for example, kaolinites, montmorillonites and micas; calcium carbonate; calcium sulfate; synthetic hydrated silicon oxides and synthetic calcium or aluminum silicates; elements such as, for example, carbon and sulfur; natural and synthetic resins such as, for example, coumarone resins, polyvinyl chloride and styrene polymers and copolymers; bitumen; waxes such as, for example, beeswax, paraffin wax, and chlorinated mineral waxes; solid fertilizers, for example, superphosphates; and ground, naturally-occurring, fibrous materials, such as ground corncobs.

Examples of suitable fluid carriers are water; alcohols, such as for example, isopropyl alcohol; glycols; ketones such as for example, acetone, methyl ethyl ketone, methyl isobutyl ketone, isophorone and cyclohexanone; ethers, such as, for example, cellosolves; aromatic hydrocarbons such as for example, benzene, toluene and xylene; petroleum fractions such as for example, kerosene, light mineral oils; chlorinated hydrocarbons, such as for example, carbon tetrachloride, perchloroethylene, trichloroethane, including liquefied, normally vaporous, gaseous compounds. Mixtures of different liquids are often suitable.

The surface-active agent may be an emulsifying agent or a dispersing agent or a wetting agent; it may be nonionic or ionic. Any of the surface-active agents usually applied in formulating herbicides or insecticides may be used. Examples of suitable surface-active agents are the sodium or calcium salts of polyacrylic acids and lignin sulfonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; condensates of these with ethylene oxide and/or propylene oxide; condensation products of fatty alcohols or alkyl phenols, for example, p-octylphenol or p-octylcresol, with ethylene oxide and/or propylene oxide; sulfates or sulfonates of these condensation products, alkali or alkaline earth metal salts, preferably sodium salts, or sulfuric or sulfonic acid esters containing at least 10 carbon atoms in the molecule, for example, sodium lauryl sulfate, sodium secondary alkyl sulfates, sodium salts of sulfonated castor oil, and sodium alkyl-aryl sulfonates such as sodium dodecylbenzene sulfonate; and polymers of ethylene oxide and copolymers of ethylene oxide and propylene oxides.

The compositions of the invention may be prepared as wettable powders, dusts, granules, solutions, emulsifiable concentrates, emulsions, suspension concentrates and aerosols. Wettable powders are usually compounded to contain 25, 50 or 75% by weight of the active compound and usually contain, in addition to the solid carrier, 3–10% by weight of a dispersing agent, 15% of a surface-active agent and where necessary, 0–10% by weight of stabilizer(s) and/or other additives such as penetrants or stickers. Dusts are usually formulated as a dust concentrate having a similar composition to that of a wettable powder but without a dispersant or surface-active agent, and are diluted in the field with further solid carrier to give a composition usually containing 0.5–10% by weight of the active compound. Granules are usually prepared to have a size between 10 and 100 BS mesh (1.676–0.152 mm), and may be manufactured by agglomeration or impregnation techniques. Generally, granules will contain 0.5–25% by weight of the active compound, 0–1% by weight of additives such as stabilizers, slow release modifiers and binding agents. Emulsifiable concentrates usually contain, in addition to the solvent and, when necessary, cosolvent, 10–50% weight per volume of the active compound, 2–20% weight per volume emulsifiers and 0–20% weight per volume of appropriate additives such as stabilizers, penetrants and corrosion inhibitors. Suspension concentrates are compounded so as to obtain a stable, non-sedimenting, flowable product and usually contain 10–75% weight of the active compound, 0.5–5% weight of dispersing agents, 1–5% of surface-active agent, 0.1–10% weight of suspending agents, such as defoamers, corrosion inhibitors, stabilizers, penetrants and stickers, and as carrier, water or an organic liquid in which the active compound is substantially insoluble; certain organic solids or inorganic salts may be dissolved in the carrier to assist in preventing sedimentation or as antifreeze agents for water.

Aqueous dispersions and emulsions, for example, compositions obtained by diluting a wettable powder or a concentrate according to the invention with water, also lie within the scope of the present invention. The said emulsions may be of the water-in-oil or of the oil-in-water type, and may have a thick, mayonnaise-like consistency.

The compositions of the invention may also contain other ingredients, for example, other compounds possessing pesticidal, especially insecticidal, acaricidal, herbicidal or fungicidal properties, as are appropriate to the intended purpose.

Growth regulator or protection of a locus or area from undesirable plants is effected by applying a compound of Formula I, ordinarily in a composition of one of the aforementioned types, to soil in which the seeds of the unwanted plants are present, or to the foliage of the unwanted plants. The active compound, of course, is applied in an amount sufficient to exert the desired action.

The amount of the compound of the invention to be used in regulating plant growth, including combating undesired plants, will naturally depend on the condition of the plants, the degree of activity desired, the formulation used, the mode of application, the climate, the season of the year, and other variables. Recommendations as to precise amounts are, therefore, not possible. In general, however, application to the locus to be protected of from 0.1 to 10.0 kg per hectare of the compound of Formula I will be satisfactory.

EXAMPLES OF ACTIVITY WITH RESPECT TO PLANTS

In the following examples, the species of plants that were tested were:
Barnyardgrass (watergrass)—*Enchinochloa crus-galli*
Large crabgrass—*Digitaria sanguinalis*
Downy brome—*Bromus tectorum*
Yellow foxtail—*Setaria lutescens*
Redroot pigweed—*Amaranthus retroflexus*
Sicklepod—*Cassia obtusifolia*
Velvetleaf—*Abutilon theophrasti*
Garden cress—*Lepidium sativum*
Johnsongrass—*Sorghum halepense*
Mustard—*Brassica kaber*
Grain sorghum—*Sorghum vulgare* (Pioneer 265)
Corn—*Zea maize* (deKalb X363)
Cotton—*Gossypium hirsutum* (Acala SJ-2)
Soybean—*Glycine max* (Amsoy 71)
Wheat—*Triticum aestivum* (Cajeme 71)
Sugar beet—*Beta vulgaris*
Cocklebur—*Xanthum pennsylvanicum*

PRIMARY TESTS—PREEMERGENCE ACTIVITY

The preemergence (soil) activity of compounds of the invention was evaluated by planting seeds of barnyardgrass, garden cress, downy brome, velvetleaf, yellow foxtail, and sicklepod in test tubes, nominally measuring 25×200 mm, filled about three-quarters full of untreated soil, in each case covered on top with about 2.5 cubic centimeters of soil treated with a certain amount of the test compound. The treated soil applied to the tubes containing the barnyardgrass and cress seeds contained one milligram of the test compound per tube, and contained 0.1 mg of the test compound per each tube containing the seeds of the other plants. The dosages were approximately 22 and 2.2 lb of test compound per acre, respectively. The seeds were planted on top of the treated soil and covered with about 1.5 cubic centimeters of untreated soil. The planted soil was held under controlled conditions of temperature, moisture, and light for 9 to 10 days. The amounts of germination and growth in each tube were evaluated on a 0 to 9 scale, the numeric ratings having the following meanings:

| Rating | Meaning |
| --- | --- |
| 9 | No living tissue |
| 8 | Plant severely damaged and expected to die |
| 7 | Plant badly damaged, but expected to live |
| 6 | Moderate damage, but complete recovery expected |
| 5 | Intermediate damage (probably unacceptable for crop plants) |
| 3–4 | Observable damage |
| 1–2 | Plant slightly affected, possibly by the chemical, possibly due to biological variability |
| 0 | No visible effect |

PRIMARY TESTS—POSTEMERGENCE ACTIVITY

The postemergence (foliar) activity of compounds of the invention was evaluated by spraying 10-day-old large crabgrass plants, 13-day-old redroot pigweed plants, 6-day-old Johnsongrass plants, 9-day-old velvetleaf plants, 9-day-old yellow foxtail plants and 9-day-old sicklepod plants to runoff with a liquid formulation of the test compound. The crabgrass and pigweed plants were sprayed with 2.4 ml of a 0.25% solution (about 10 lb of the test compound per acre), and other plants were sprayed with 2.4 ml of a 0.025% solution (about 1 lb of the test compound per acre). The sprayed plants were held under controlled conditions of temperature, moisture and light for 7 to 8 days, and the effect of the test compound was then evaluated visually, the results being rated on the 0 to 9 scale described above.

Results of the preemergence and postemergence activity tests conducted on the compounds of the invention are set forth in Table II.

TABLE II

| Embodiment | Preemergence (soil) | | | | | | Postemergence (Foliar) | | | | | |
|---|---|---|---|---|---|---|---|---|---|---|---|---|
| | Barnyard-grass | Garden Cress | Downy Brome | Velvet-leaf | Yellow Foxtail | Sickle-pod | Crab-grass | Pig-weed | Johnson-grass | Velvet-leaf | Yellow Foxtail | Sicklepod |
| XIII | 8 | 7 | 7 | 3 | 7 | 2 | 4 | 2 | 2 | 0 | 0 | 0 |
| III | 9 | 8 | 8 | 3 | 8 | 2 | 7 | 3 | 0 | 2 | 0 | 0 |
| IV | 9 | 8 | 8 | 3 | 8 | 5 | 0 | 0 | 0 | 0 | 0 | 0 |
| V | 9 | 8 | 7 | 3 | 8 | 4 | 3 | 2 | 0 | 0 | 0 | 0 |
| VI | 8 | 7 | 6 | 3 | 7 | 5 | 4 | 3 | 2 | 3 | 0 | 2 |

What is claimed is:

1. A compound of the formula

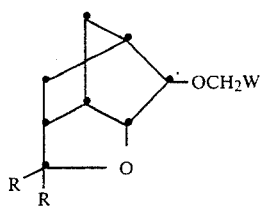

wherein each R independently is a hydrogen atom or an alkyl group containing from 1 to 6 carbon atoms; and W is an ethynyl group, a cyano group, a cyclohexenyl group or a phenyl group optionally substituted by 1 or 2 chlorine or fluorine atoms or methyl groups, a cycloalkyl group containing 3 to 10 carbon atoms, a secondary alkyl group containing 3 to 10 carbon atoms, or a heterocyclic group selected from an imidazolyl, a triazolyl, thiadiazolyl, 2-quinolinyl, 1-isoquinolinyl, pyrrolyl, N-methylimidazol-2-yl, N-methylpyrazol-2-yl, isoxazolyl, oxazolyl, isothiazolyl, thiazolyl, thienyl, 5-methyl-2-furanyl, 2-pyridinyl or 3-pyridazinyl group.

2. A compound according to claim 1 wherein W is an ethynyl group, a 2-pyridinyl group or a phenyl group optionally substituted by 1 or 2 chlorine or fluorine atoms or methyl groups.

3. A compound according to claim 2 wherein each R is independently a hydrogen atom or a methyl group.

4. A compound according to claim 3 wherein each R is a hydrogen atom.

5. A compound according to claim 4 wherein W is a 2,6-dichlorophenyl group.

6. A compound according to claim 4 wherein W is a 2-fluorophenyl group.

7. A compound according to claim 4 wherein W is a phenyl group.

8. A compound according to claim 4 wherein W is a 2-methylphenyl group.

9. A composition for controlling plant growth comprises an effective amount of a compound according to claim 1 and at least one surface-active agent or carrier.

10. A method of controlling undesirable plant growth at a locus comprises applying to the locus or the plant an effective amount of a compound according to claim 1.

11. A method according to claim 10 wherein the control is depressing the growth of or killing the plant.

* * * * *